United States Patent [19]

Nance

[11] Patent Number: 4,643,754

[45] Date of Patent: Feb. 17, 1987

[54] ADDITIVE FOR INHIBITING RESPIRATION OF AND PROMOTING DESICCATION OF CROPS

[75] Inventor: Kenneth H. Nance, Bromley, England

[73] Assignee: BP Chemicals Limited, London, England

[21] Appl. No.: 862,671

[22] Filed: May 13, 1986

[30] Foreign Application Priority Data

May 18, 1985 [GB] United Kingdom ............... 8512634

[51] Int. Cl.$^4$ ............................................ A01N 59/00
[52] U.S. Cl. ............................................ 71/1; 71/69; 71/84
[58] Field of Search ...................... 71/1, 65, 69, 84

[56] References Cited

U.S. PATENT DOCUMENTS

| | | | |
|---|---|---|---|
| 3,447,919 | 6/1969 | Young | 71/69 |
| 3,450,519 | 6/1969 | Stoller | 71/69 |

*Primary Examiner*—Ferris H. Lander
*Attorney, Agent, or Firm*—Brooks Haidt Haffner & Delahunty

[57] ABSTRACT

This invention relates to a process for applying an aqueous solution comprising formate anions and a cation selected from sodium, potassium and calcium to a crop to inhibit respiration of the crop and to accelerate desiccation thereof. The aqueous solution contains the anions and cations in a ratio of at least 4:1 on a chemical equivalent basis. Aqueous solutions of potassium pentaformate or hexaformate are preferred. The process uses relatively non toxic materials, reduces dry matter loss and accelerates drying.

7 Claims, No Drawings

ADDITIVE FOR INHIBITING RESPIRATION OF AND PROMOTING DESICCATION OF CROPS

The present invention relates to an improved method of inhibiting plant respiration and facilitating drying prior to harvest by use of specific chemical additives.

The need to dry crops rapidly after they have been cut is well recognised. This is due to the fact that although the photo-respiration of the plant ceases upon cutting, the catabolic process involving the oxidation of plant sugars to carbon dioxide continues. The energy generated by this oxidation appears as heat which together with the mositure content accelerates the destruction of the plant sugars and hence its nutrients. In addition rapid drying is also important because the cut crop must be harvested within a short period to inhibit respiration of the crop and thereby minimise loss of dry matter. The slow rate at which forage crops normally dry after cutting may lead to as much as 30% loss of dry matter e.g. during haymaking according to Klinner, W E, Paper No. 2 entitled "The field treatment of grass for conservation" presented at the "Annular Conference of the Institute of Agricultural Engineers" (1976).

Physical, mechanical and chemical methods have been used to accelerate drying of forage crops. The physical methods used are usually capital and energy intensive and not all farmers employ them. Hence chemical treatment of the crops is an interesting alternative or additional treatment. Of the chemicals tried hitherto chloroform, petroleum ether, formic acid and organo-phosphorus compounds have been used with some degree of success. These chemicals are believed to dissolve or damage the impervious waxy layer (cuticle) covering the plant or crop thereby facilitating the loss of moisture. However, there are obvious volatility problems with the use of compounds such as chloroform and petroleum-ether, whereas free formic acid is highly corrosive and unpleasant to handle.

Moreover, chloroform and petroleum ether only accelerate drying but do not inhibit respiration or prevent the consequent loss of dry matter. On the other hand, formic acid only inhibits respiration and reduces loss of dry matter, and does not accelerate drying to the same extent as chloroform or petroleum ether.

In contrast some organo-phosphorus compounds e.g. tri-n-butyl phosphate both inhibit respiration, measured as oxygen uptake, and reduce dry matter losses according to Harris, C E, in J. Agricultural Science, Cambridge (1978) 91, 185–189. However organo-phosphorus compounds interfere with the metabolic processes of (a) the plants or crops being treated and consequently (b) the animals consuming the treated crops or plants. These organo-phosphorus compounds are therefore of limited use only.

It has been found that the problem of respiration and dry matter loss can be overcome with the simultaneous acceleration of drying using a single additive which is free from the drawbacks of the additives used hitherto.

Accordingly, the present invention is a process for drying and inhibiting the respiration of crops by applying to the crops an aqueous solution comprising formate anions and a cation selected from potassium, sodium and calcium ions in a chemical equivalent ratio greater than 4:1. Cations of potassium are particularly preferred.

The aqueous solution applied to the crop suitably contains formate anions to potassium cations in a chemical equivalent ratio of at least 5:1, preferably 6:1. Specifically, the potassium ions and formate ions may be present as a complex acid salt e.g. potassium tetrahydrogen formate (hereafter referred to as "potassium pentaformate") or potassium pentahydrogen formate (hereinafter referred to as "potassium hexaformate")

The aqueous solution used suitably has from 1 to 75% w/w of the complex acid salt, preferably from 1 to 25% w/w, most preferably from 2–10% w/w.

The amount of the aqueous solution of the complex acid salts used will depend upon the nature of the complex acid salt used, the crop and the moisture content thereof. It is suitably applied to the crop at a rate of 0.5 to 10% w/w on fresh crop treated, preferably from 1 to 5% w/w.

The aqueous solution containing the complex acid salt may be applied on the crop by conventional spraying techniques either prior to cutting, while cutting or conditioning and up to 30 minutes after cutting i.e. while tedding.

The presence of potassium ions in the aqueous solution used has a positive advantage because it prevents the closure of the stomata in the leaves and stems thereby accelerating drying of the crop. This also enables the formate ion to have access to the inner cells of the crop being treated thereby improving the inhibitory effect on its respiration.

The aqueous solution containing the potassium ions and formate ions, whether or not introduced as a complex acid salt may contain other suitable adjuvants.

For instance these may be grouped as follows:

(a) Low volatility acidic materials to lower the pH to enhance the effect of the antirespirant or biostat through lowering the pH., i.e. acetic acid, propionic acid, butyric acid, succinic acid, valeric acid, glutaric acid, laevulinic acid, sorbic acid, phosphoric acid and sulphuric acid, permitted food acidulants.

(b) Materials added to obtain other benefits i.e. mould inhibitors which are salts of $C_2$–$C_8$ carboxylic acids.

(c) Minerals in trace amounts of overcome deficiencies in forages e.g. copper, selenium, magnesium.

(d) Surfactants to reduce surface tension and improve distribution of desiccant.

(e) Mineral oils, hydrocarbon oils, vegetable oils etc to reduce losses of the formates applied due to evaporation and/or leaching by water such as e.g. rain or irrigation.

The present invention is further illustrated with references to the following Examples:

EXAMPLES

1. RESPIRATION

The method used for testing the performance of the complex acid salt solutions relies on the measurement of $CO_2$ produced as a result of fungal respiration. This is contained within the air used for drying and is measured using a continuous recording instrument. $CO_2$ is a primary product of metabolism which can be easily and accurately determined without disturbing the drying crop.

Table 1 below shows the relative respiration rates of grass and of grass treated with three additives at 0.4%. These are formic acid, potassium formate and potassium hexaformate. The moisture contents at the start and finish of each run are also indicated.

The tests shown in Table 1 used 100 gms of grass and 20 liters per minute of air in a transparent perspex tube of 150 mm diameter. Carbon dioxide was measured continuously and the tubes were weighed before and after the experiment to determine the loss of volatile matter.

From Table 1 the superiority of the hexaformate over the other materials can be seen. In other runs the effectiveness of the compositions of the present invention were also compared with potassium tetra-formate and potassium penta-formate. Potassium hexaformate was also mixed with equal parts of formic acid and with 25% by weight of formic acid and the effects studied. At no time were any of these found to be more effective than potassium hexaformate alone at this level of application.

TABLE 1

RESPIRATION OF GRASS

Rate of Respiration over a duration of hours based on gms of $CO_2$ liberated per hour per kilogram of dry matter treated

| Additive | Hours | | | |
|---|---|---|---|---|
| | 0 | 24 | 36 | 48 |
| | $CO_2$ liberated gms | | | |
| None | 2.5 | 1.0 | 0.62 | — |
| Formic Acid | 1.8 | 0.7 | 0.52 | 0.48 |
| Potassium Formate | 1.2 | 0.5 | 0.38 | 0.27 |
| Potassium Hexaformate | 0.9 | 0.46 | 0.27 | 0.25 |

2. DESICCATION TESTS

The desiccation effects of using the complex acid formate salts in the present invention was tested as follows:

The tests were carried out on
(a) freshly cut grass alone,
(b) freshly cut grass which was mechanically conditioned, i.e. abraded to simulate exposure of the cuticles and,
(c) freshly cut grass which was mechanically conditioned as in (b) above and then chemically conditioned using an aqueous solution of potassium hexaformate (0.2% w/w of the acid salt based on the fresh cut wet grass).

The cut and treated materials were weighed in the laboratory for dry matter after leaving them in the field for 3 hours and 6 hours respectively. The results are tabulated in Table 2 below.

TABLE 2

| Test | Dry Matter content After | |
|---|---|---|
| | 3 hours | 6 hours |
| (a) | 20% | 28% |
| (b) | 25% | 34% |
| (c) | 30% | 43% |

The above tests show that the complex acid salts used in the present invention inhibit respiration and promote desiccation as claimed.

I claim:

1. A process for drying and inhibiting the respiration of crops by applying to the crops an aqueous solution comprising formate anions and a cation selected from potassium, sodium and calcium ions in a chemical equivalent ratio greater than 4:1.

2. A process according to claim 1 wherein the formate anions and the cations in the aqueous solution are derived from a complex acid salt of the anions with the cations.

3. A process according to claim 1 wherein the complex acid salt is a tetrahydrogen formate or a pentahydrogen formate of potassium, sodium or calcium.

4. A process according to claim 3 wherein the amount of complex tetrahydrogen or pentahydrogen formate in aqueous solution applied to the crop is from 0.01–10% w/w of the total crop treated.

5. A process according to claim 4 wherein the aqueous solution applied to the crops comprises potassium tetrahydrogen formate or potassium pentahydrogen formate.

6. A process according to claim 1 or 2 wherein the aqueous solution of the formate is applied to the crop prior to cutting, during cutting or conditioning, or while tedding.

7. A process according to claim 1 or 2 wherein the aqueous solution contains in addition one or more of the following adjuvants:
   (a) pH lowering agents selected from phosphoric acid, succinic acid, valeric acid, glutaric acid, laevulinic acid, sorbic acid and sulphuric acid;
   (b) mould inhibitors which are salts of $C_2$–$C_8$ carboxylic acids;
   (c) trace amounts of mineral metals selected from copper, selenium and tellurium;
   (d) surfactants to reduce surface tension and improve distribution of desiccant; and
   (e) mineral oils, hydrocarbon oils or vegetable oils to reduce losses of the formates applied due to evaporation and/or leaching by water.

* * * * *

UNITED STATES PATENT AND TRADEMARK OFFICE
CERTIFICATE OF CORRECTION

PATENT NO. : 4,643,754
DATED : February 17, 1987
INVENTOR(S) : Kenneth Horace Nance It is certified that error appears in the above-identified patent and that said Letters Patent is hereby corrected as shown below:

Col. 1, line 23, ""Annular" should read -- "Annual --

Col. 1, line 50, "91" should read --$\underline{91}$ --

Col. 1, line 56, "It has been found" should read --It has now been found --

Signed and Sealed this

Second Day of June, 1987

Attest:

DONALD J. QUIGG

Attesting Officer

Commissioner of Patents and Trademarks